United States Patent [19]
Huber et al.

[11] Patent Number: 5,776,598
[45] Date of Patent: Jul. 7, 1998

[54] FIBRE TREATMENT

[75] Inventors: Bernd Huber; Gerhard Stein, both of Kelheim; Heinz Paul Pöter, Saal, all of Germany; David Eric William Hill, Grimsby, Germany

[73] Assignee: Faserwerk Kelheim GmbH, Germany

[21] Appl. No.: 601,215

[22] Filed: Jan. 30, 1996

[30] Foreign Application Priority Data

Jan. 31, 1995 [GB] United Kingdom ............... 9501845

[51] Int. Cl.⁶ ............................ B32B 5/06; B32B 5/22
[52] U.S. Cl. .................. 428/298; 106/243; 106/244; 427/23; 427/2.31; 427/342; 427/421; 428/302; 428/393
[58] Field of Search ..................... 106/243, 244; 427/2.3, 2.31, 340, 341, 342, 421; 428/298, 302, 393

[56] References Cited

U.S. PATENT DOCUMENTS 3,108,011  10/1963  Frotscher .................. 427/342 X

FOREIGN PATENT DOCUMENTS 395099  10/1990  European Pat. Off. .

Primary Examiner—Michael Lusignan
Attorney, Agent, or Firm—Howson and Howson

[57] ABSTRACT

A method of treating a surface of a fiber, e.g. cellulosic fiber, with a finish in which the surface finish is applied as an aqueous emulsion stabilized at a first pH value and at the latest when applied to the fiber the emulsion is caused to destabilize by a change in the first pH value. The invention also relates to cellulosic fiber and threads thereof and to tampons made from cellulosic fiber.

9 Claims, 1 Drawing Sheet

FIBRE TREATMENT

BACKGROUND OF THE INVENTION

This invention relates to the treatment of fibre surfaces with finishes applied from aqueous emulsions, and to a means of stabilising an aqueous emulsion.

The invention is particularly useful in the treatment of cellulosic fibres, especially fibre produced by the viscose process. In EP-A-0395099 there is described the use of mixtures of monoesters and diesters of polyhydric aliphatic alcohols and fatty acids as treatment on absorbent material for the amelioration of toxic shock syndrome, when the absorbent material is utilised in tampons. The preferred monoester is glycerol monolaurate (GML) and the preferred diester is glycerol dilaurate (GDL), with the mixture preferably comprising at least 93% GML.

During fibre production the processing agents affecting the properties of the fibres are usually applied to the fibre surfaces during the finishing stages. Typically in the processing of natural fibres such as cotton, or semi-synthetic cellulosic fibres or threads, the fibre processing agents are usually applied as aqueous solutions or emulsions.

In addition to processing agents, which normally affect subsequent processing properties, it is also possible to apply components which have, for example, a biological or medicinal action. These include, for example, the suppression of bacterial growth which decomposes perspiration and causes perspiration odour, or the application of medicinal active ingredients, for example in the form of ointments, to non-wovens, knits or fabrics for medical treatment. In such cases, it may be necessary to apply relatively large quantities of active ingredient, for example between 0.3 and 50% by weight, based on the weight of fibres.

Since many of these components, including GML for the amelioration of toxic shock syndrome, are not water-soluble, emulsifiers are used to make stable aqueous emulsions which ensure an even application to the fibre surfaces. Emulsions which have proved particularly successful in this instance are "microemulsions" where the emulsified particles are so fine that the entire emulsion appears clear and transparent. Standard emulsions, on the other hand, are milky and turbid.

Where active ingredients are to be applied, however, the addition of emulsifiers is usually undesirable since these may affect the biological and/or medicinal action or may result in undesirable side-effects. Furthermore, the addition of a new component to the active ingredient usually requires a new licence from the appropriate government authorities. This takes up a great deal of time and resources.

Glycerol monolaurate is insoluble in water. If the substance is melted in hot water and dispersed under vigorous stirring, the result is a white, milky, viscous to highly viscous dispersion which is not stable in storage and from which the glycerol monolaurate separates out again (skims off).

A dispersion of this kind is not very suitable for a fibre finishing process, since the coarsely dispersed, and rapidly decomposing dispersion results in a very uneven application and uneven distribution on the fibre surfaces. An even application is, however, important for a safe medicinal action so as to ensure the minimum active concentration throughout the products in one production batch. With an uneven application, the quantity applied must be considerably overdosed to ensure a minimum concentration.

Since GML is difficult to get into a stable aqueous emulsion it is usually applied from an isopropyl alcohol solution as described in EP-A-0395099. However, the use of solvent is undesirable for cost and health reasons.

SUMMARY OF THE INVENTION

The present invention provides a means of forming a stable aqueous emulsion of an ester of a polyhydric aliphatic alcohol and a fatty acid, in particular a mixture of GML and GDL, and of applying the emulsion to fibres in concentrations in excess of 0.3% by weight, and preferably over 10% by weight.

DETAILED DESCRIPTION OF THE INVENTION

Figure 1:
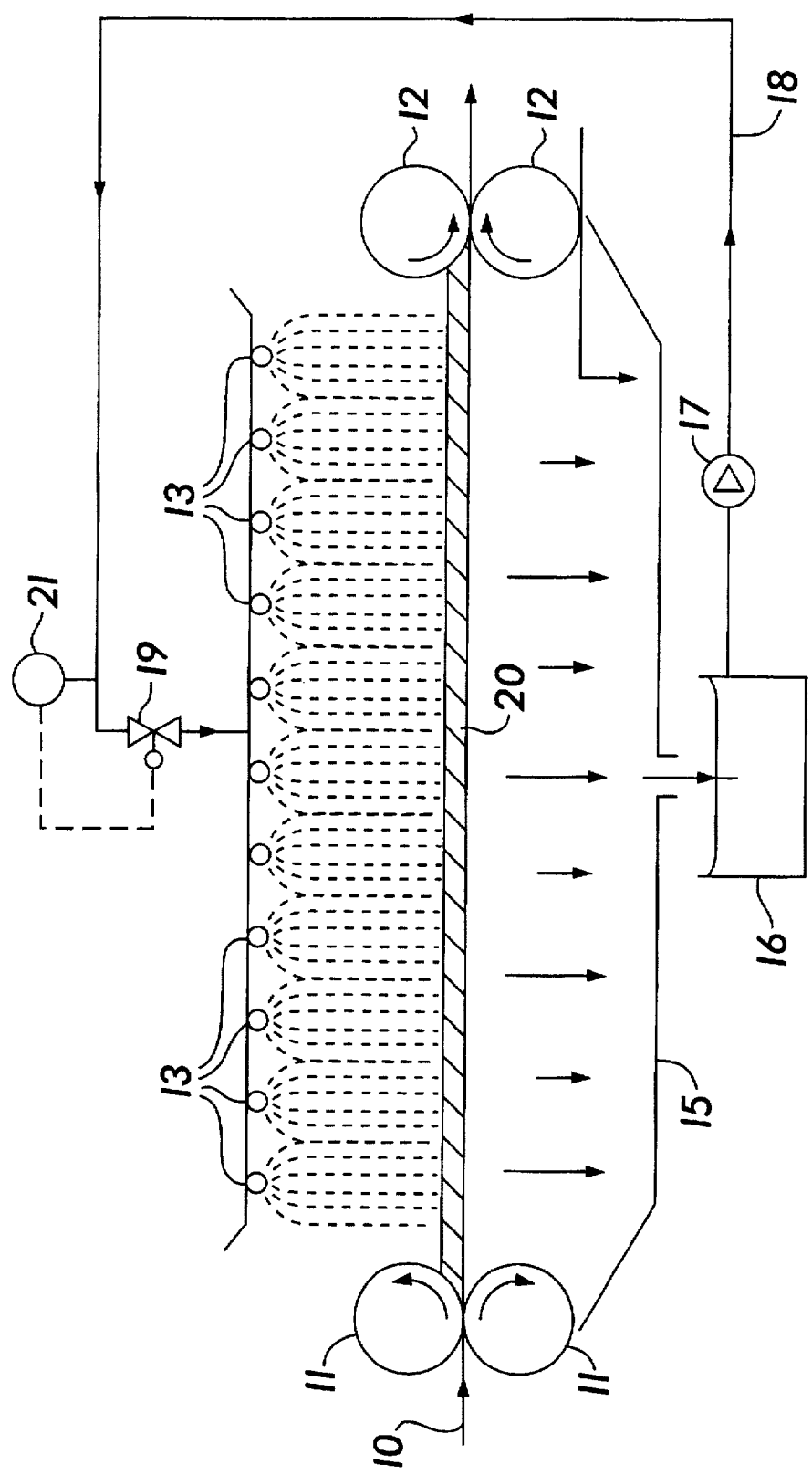
FIG. 1 is a schematic view of the finish system which is entered by the fibres from the wash bed.

According to the invention there is provided a method of treatment of a fibre surface with a finish in which the surface finish is applied as an aqueous emulsion stabilised at a first pH value and at the latest when applied to the fibre the emulsion is caused to destabilise by a change in said first pH value.

The pH change may be brought about either by the fibre having a residual pH different to that of the emulsion, or by the addition of acid or alkali to the emulsion prior (e.g. shortly before) to application of the emulsion to the fibre.

Also according to the invention there is provided a method of producing a stable aqueous emulsion of a carboxylic acid ester without the use of an additional emulsifying agent wherein said method comprises mixing the ester with water, and neutralising any free acid present by means of an alkaline solution.

It is surprising that a stable emulsion, typically a micro emulsion, can be obtained merely by neutralising any free acid present in the ester.

Preferably the emulsion contains a carboxylic acid ester mixture comprising monoesters and diesters of polyhydric aliphatic alcohols and fatty acids, and preferably is predominantly an emulsion of GML.

Conveniently the method is used for the surface treatment of cellulosic fibres and in particular cellulose made by the viscose process, and the solvent spun cellulose known as lyocell.

The cellulose fibres which have been surface treated by GML are particularly suitable for the manufacture of tampons.

With a method as described in the present invention it is possible to convert the glycerol monolaurate into a low-viscosity microemulsion which is stable in storage without the addition of emulsifiers.

The present invention is likewise based on a method of producing fibres coated with very large quantities of glycerol monolaurate (i.e. concentrations in excess of 3% by weight, preferably over 10% by weight, based on the weight of fibres).

Even after purification by distillation, glycerol monolaurate contains small quantities of free lauric acid. This quantity of lauric acid can be determined by acid titration. If this quantity of free acid is neutralised in an aqueous suspension with an equivalent quantity of alkaline solution, for example a potassium or sodium hydroxide solution, without further additives, this product can be converted into a low-viscosity transparent virtually water-clear microemulsion which is stable in storage. It is recommended at this point that the emulsion be stored at a temperature above 50 degrees Celsius, since below this temperature viscosity rises sharply and turbidity increases.

Since processing agents are normally always applied at elevated temperatures, however, this does not constitute a disadvantage.

The preparation of the stable emulsion will be described hereinafter with reference to the following Examples:

EXAMPLE 1
Determination of the acid number 100 g of glycerol monolaurate (trade name Monomuls 90-L 12 produced by Henkel KGaA) was dissolved in 600 ml of methanol and mixed with enough water to produce slight, permanent turbidity. The solution was then titrated with lnNaOH to the turning point of the pH titration curve 2.3 ml of lnNaOH were used.

EXAMPLE 2
Emulsifying test 1 (comparison)

100 g of glycerol monolaurate were mixed into 900 ml of water at 60 degrees Celsius under vigorous stirring. A short time after the stirring was discontinued, 2 phases separated.

EXAMPLE 3
Emulsifying test 2

100 g of glycerol monolaurate were mixed into 900 ml of water at 60 degrees Celsius under vigorous stirring. 1 ml of lnNaOH having been added to the water. After stirring had been discontinued the emulsion was more stable than in Example 1 but phase separation occurred over a period of some hours.

EXAMPLE 4
Emulsifying test 3

100 g of glycerol monolaurate were mixed into 900 ml of water at 60 degrees Celsius under vigorous stirring, 2 ml of lnNaOH having been added to the water. This produced a virtually clear emulsion which was stable after 96 hours even after storage at 60 degrees Celsius.

EXAMPLE 5
Emulsifying test 4

100 g of glycerol monolaurate were mixed into 900 ml of water at 60 degrees Celsius under vigorous stirring, 2.3 ml of lnNaOH having been added to the water. This produced a virtually clear emulsion which was stable after 96 hours even after storage at 60 degrees Celsius.

EXAMPLE 6
Emulsifying test 5

100 g of glycerol monolaurate were mixed into 900 ml of water at 60 degrees Celsius under vigorous stirring, 3 ml of lnNaOH having been added to the water. When the compound was stirred in, the mixture became much more viscous than in Examples 2 to 5, stirring-in was more difficult, and flowability and pumpability were much poorer than in Examples 4 and 5.

EXAMPLE 7
Emulsifying test 6

100 g of glycerol monolaurate were mixed into 900 ml of water at 60 degrees Celsius under vigorous stirring, 4 ml of lnNaOH having been added to the water. When the compound was stirred in, the mixture became highly viscous, intermixing during stirring-in was poor and flowability and pumpability were even poorer than in Example 6.

These Examples show that if insufficient alkali is added as per Example 3, or excess alkali is added as in Example 6, during the neutralisation such that the free acid is not substantially neutralised, or the emulsion becomes alkaline, then the emulsions produced are usable but differ in stability, clarity, and viscosity from the equimolar quantities (Example 5) or the substantially neutralised emulsion as per Example 4. In extreme pH conditions (such as Examples 2 and 7) the emulsions are either too unstable or are too viscous to be usable.

With the aid of the method of the invention it is possible to produce concentrated stock mixes that can be used in the fibre production process. Stock mixed with 50 and 100 g/l have been used successfully; higher concentrations can be produced where these are required.

The emulsions are preferably prepared as per Example 5 at 60–80 degrees Celsius and stored at 60 degrees prior to being added to the fibre finishing process. The solutions prepared in this way are stable over a period of several days, and no decomposition was observed even after a relatively long period. Higher temperatures can also be used. If a solution at 60 degrees is cooled to a lower temperature, the viscosity of the emulsion increases sharply after some time, and flowability and pumpability are very adversely affected. Reheating restores the good level of usability.

The application of the GML emulsions to the viscose fibres will be described by way of further examples and with reference to the accompanying drawing which is a schematic of a viscous fibre finish application system.

Cellulose fibre, preferably of the viscose type, is produced in a well known manner by spinning and regeneration of the cellulose in an acid bath. The fibres are then cut and washed to produce staple fibres.

Staple fibres from the wash beds enter the finish system on a porous belt (10) in the form of a fibre blanket (20) through the nip created by a first set of rollers (11) and exit the system through the nip created by a second set of rollers (12) arranged downstream. In a typical system the fibres pass on to a drier. The fibre blanket (20) between the two sets of rollers (11) (12) passes under spaced spray heads (13) and is sprayed by the aqueous emulsion of the finishing material (GML).

Excess emulsion passing through the blanket (20) is collected in a sump (15) and passed into a holding tank (16) of a recirculation system. The emulsion in the tank is fed by a pump (17) through a conduit (18) to a valve (19) which meters the aqueous emulsion to the spray heads (13). The valve (19) is controlled by a flow controller device (21).

The liquid capacity of the recirculation system is between 4–5 m$^3$ and the fluid is recirculated approximately 10 times per hour with a flow rate of about 47 m$^3$ per hour.

The various mixes of GML were added to the processing agent cycle of a viscose spinning plant, preferably to the return flow in the sump (15). Spray apparatus including spaced-apart heads (13) has proved eminently suitable for an even application of the emulsion to the fibres in the blanket (20).

The finishing process for the application of GML to viscose fibres will be observed in more detail with reference to the following Examples.

EXAMPLE 8

On a viscose fibre production line with a production rate of 500 kg per hour, a processing agent sector—after washing and prior to drying—was operated as a circulating bath in which the fibres were sprayed. The circulation rate was selected so that the entire volume of liquid finish was circulated approximately 10 times per hour. The temperature of the liquid was kept at 55 to 60 degrees Celsius. The moisture content of the fibres on the discharge side was approximately 10% higher than on the inlet side. A stock solution with 10% by weight of glycerol monolaurate, prepared in accordance with Example 5, was added to the return flow of the finish cycle via the sump (15) at a rate of 16 kg per hour. The pH value of the bath was 7, to 7.5.

The glycerol monolaurate content of the fibres in the blanket (20) leaving the second set of rollers (12) was 0.3% by weight. The concentration differences of the processing agent between the intake and return flow of the treatment cycle were small.

EXAMPLE 9

Fibres were produced in the same way as in Example 8. The pH of the liquid in the processing agent cycle was adjusted to be between 4 and 5 with sulphuric acid. After the blanket (20) of non-woven fibres had passed through, only small quantities of glycerol monolaurate were detectable in liquid draining into the sump (15). This meant that the concentration in the intake was much lower than in Example 8. The whole quantity of glycerol monolaurate added was absorbed by the fibres as it passed through the non-woven blanket (20). The glycerol monolaurate content of the fibres leaving the rollers (12) was again 0.3% by weight.

EXAMPLE 10

Fibres were produced in the same way as in Example 8. The amount of glycerol monolaurate stock solution added to the sump (15) was increased from 16 kg per hour to 65 kg per hour. After the liquid had passed through the non-woven blanket (20) only small quantities of glycerol monolaurate were detectable in it. The glycerol monolaurate content of the fibres leaving the rollers (12) was 1.2% by weight.

EXAMPLE 11

Fibres were produced in the same way as in Example 8. The amount of glycerol monolaurate stock solution added to the sump (15) was increased briefly from the 16 Kg per hour quantity of Example 8 to 1000 kg per hour. After the non-woven blanket (20) had passed through, only small quantities of glycerol monolaurate were detectable in the bath. The glycerol monolaurate content of the fibres leaving the rollers (12) was 20% by weight.

Moisture exchange causes the fibres to absorb processing agent. Absorption can be initially intensified if, prior to entering the processing agent sector, the fibre is pressed to a greater extent by the nip at the inlet rollers (11) than on the discharge side by the nip at the exit rollers (12). The higher absorption will continue until the system reaches equilibrium conditions. The quantity of finish to be applied is calculated under equilibrium conditions from the fibre throughput and the quantity of processing agent added.

Coatings achievable with this process under commercial conditions as illustrated in Example 8 are limited to quantities less than or equal to 5% by weight based on the weight of fibres. The cellulosic fibres have a residual slightly acid pH value of about pH 6 and it is the contact of the substantially neutral GML emulsion with the slightly acidic fibres that cause the GML to deposit onto the fibres.

However, it is possible to apply a much larger coating quantity of glycerol monolaurate to the fibres if the stock emulsion solution is fed into a slightly acidified processing agent cycle—preferably into the return flow. pH values of between 3 and 6, preferably 3.5 to 5, can be used for this. pH values of less than 3 can also be used but result in fibres whose pH is too acid for many applications in health care or beauty care.

The increase in acidity of the emulsion causes the emulsion to destabilize and under these conditions virtually the entire quantity of glycerol monolaurate which flows through the fibre blanket is absorbed by the fibres. The concentration in the flow returning to the sump is, at this time, well below 10% of the quantity in the intake.

In this way, it is possible to apply large active ingredient concentrations of, for example, 10 to 50% by weight, based on the weight of fibres.

The present invention describes a method of producing an emulsion of glycerol monolaurate in water, which emulsion is stable in storage, and the use of this emulsion for the application of glycerol monolaurate to fibre surfaces. By neutralising the free lauric acid which is present in traces, it is possible to produce a formulation resulting in a stable, transparent and low-viscosity microemulsion. This emulsion can be used to apply glycerol monolaurate evenly to fibre surfaces. if the emulsion is acidified shortly prior to application, substantially all glycerol monolaurate present in the emulsion can be left on the fibres. In this way, it is possible to produce precision coating quantities of 0.3 to 30% based on the weight of fibres, in a homogeneous distribution on the surface, and the quantity of GML deposited in the fibres can be made to be directly proportional to the quantity added to the stock emulsion per hour.

For example under the condition of Example 10, sample fibres from the fibre blanket (20) were removed from the top, middle and bottom thereof and the finish content measured.

The GML deposits based on dry fibre were found to be as follows:

|  | Test 1 | Test 2 |
|---|---|---|
| Top | 1.2% | 1.5% |
| Middle | 1.4% | 1.2% |
| Bottom | 1.2% | 1.2% |

It has been found that other esters of polyethylene glycol and fatty acids can also be stabilised using the same techniques.

EXAMPLE 12

Emulsifying Test 7

This test was carried out according to the conditions of Example 5, except that Peg 200 coconut fatty acid ester was substituted for GML. The coconut fatty acid ester went into a clear microemulsion.

EXAMPLE 13

Emulsifying Test 8

This test was carried out according to the conditions of Example 5 except that PEG 600 caster oil was substituted for GML. The caster oil material went into a clear microemulsion.

EXAMPLE 14

Emulsifying Test 9

PEG 600 mono-oleate was used instead of GML in condition according to Example 5. A clear microemulsion was formed.

EXAMPLE 15

Emulsifying Test 10

Carried out according to the conditions of Example 5 using Henkel EET 035 fibre treatment. It formed a clear microemulsion that was stable for several days at ambient temperatures.

EXAMPLE 16

Emulsifying Test 11 (Comparison)

This was carried out using Henkel EET 035 fibre treatment in conditions according to Example 2. The emulsion formed slowly destabilised to separate out in number of hours (less than 1 day).

We claim:

1. A method of treatment of a fibre surface with a finish comprising the steps of:

providing a surface finish as an aqueous emulsion stabilised at a first pH value;

destabilizing said aqueous emulsion by a change in said first pH value; and applying said aqueous emulsion to the fibre surface, wherein said emulsion is destabilized no later than when it is applied to the fibre surface.

2. A method as claimed in claim 1 wherein the pH changes are brought about by the fibre being at a different residual pH to the emulsion.

3. A method as claimed in claim 1 wherein the pH of the emulsion is changed by the addition thereto of acid or alkali shortly prior to application of the emulsion to the fibre.

4. A method as claimed claim 1 which is used in the surface treatment of cellulosic fibres with an aqueous emulsion of glycerol monolaurate (GML), the emulsion being stabilised by neutralising any lauric acid impurity present in the glycol monolaurate by means of an alkaline solution prior to treatment of the cellulosic fibres.

5. A method as claimed in claim 4, wherein the emulsion is added as a stock solution to the aqueous liquor used in a finishing bath cycle of a cellulose fibre spinning plant.

6. A method as claimed in claim 5, wherein the cellulosic fibres are produced in the plant by the viscose process.

7. A method as claimed in claim 5, wherein the liquor in a finishing bath cycle has a maximum first pH of 7.5, and the GML emulsion is added to a return flow in the finishing bath.

8. A method as claimed in claim 7, wherein the liquor in the finishing bath cycle has a pH in the range of between 3 and 4, and preferably between 3.5 and 5, and the quantity of GML emulsion added to the return flow is proportional to the required deposition on the fibres.

9. Cellulosic fibre and threads finished with glycerol monolaurate (GML) by means of a surface treatment as claimed in claim 4.

* * * * *

UNITED STATES PATENT AND TRADEMARK OFFICE
CERTIFICATE OF CORRECTION

PATENT NO. : 5,776,598
DATED : July 7, 1998
INVENTOR(S) : Bernd Huber, Gerhard Stein, Heinz Paul Pöter, and David Eric William Hill It is certified that error appears in the above-identified patent and that said Letters Patent is hereby corrected as shown below:

Col. 5, line 8, delete the comma after "7".

Col. 6, line 22, replace "if" with -- If --.

Col. 8, line 20, claim 8, replace "4" with -- 6 --.

Signed and Sealed this

Twenty-seventh Day of October, 1998

*Attest:*

BRUCE LEHMAN

*Attesting Officer*     *Commissioner of Patents and Trademarks*